(12) United States Patent
Zhang (10) Patent No.: US 11,834,400 B2
(45) Date of Patent: Dec. 5, 2023

(54) METHOD FOR SYNTHESIZING DIBENZOCYCLOHEPTANE DERIVATIVES BY SERIES CYCLIZATION OF FREE RADICALS UNDER ELECTROOXIDATION CONDITIONS

(71) Applicant: Zhejiang Normal University, Jinhua (CN)

(72) Inventor: Yan Zhang, Jinhua (CN)

(73) Assignee: Zhejiang Normal University, Jinhua (CN)

( * ) Notice: Subject to any disclaimer, the term of this patent is extended or adjusted under 35 U.S.C. 154(b) by 0 days.

(21) Appl. No.: 17/954,591

(22) Filed: Sep. 28, 2022

(65) Prior Publication Data

US 2023/0234907 A1 Jul. 27, 2023

(51) Int. Cl.
*C07C 49/323* (2006.01)
(52) U.S. Cl.
CPC .................... *C07C 49/323* (2013.01)
(58) Field of Classification Search
CPC ..................................... C07C 49/323
USPC .......................................... 568/308
See application file for complete search history.

(56) References Cited

U.S. PATENT DOCUMENTS

2015/0344411 A1  12/2015  Green

FOREIGN PATENT DOCUMENTS

CN    110055549 A   7/2019
CN    112175004 A   1/2021

OTHER PUBLICATIONS

Raji et al. Journal of Organic Chemistry (2021), 86(23), 17071-17081.*

* cited by examiner

*Primary Examiner* — Ana Z Muresan (57) ABSTRACT

Disclosed is a method for synthesizing dibenzcycloheptanone derivatives by series cyclization of free radicals under electrooxidation conditions, belonging to the technical field of organic synthesis. The disclosed method includes: taking o-propionyl biphenyl analogues and sodium benzenesulfinate analogues as raw materials, and electrifying and reacting the raw materials in an electrolytic cell to obtain dibenzocycloheptane derivatives. According to the application, benzenesulfinate anion is oxidized into benzenesulfonyl radical under the condition of constant current and electrolyte, then the radical attacks the a-position of alkynone reactant carbonyl to obtain an alkenyl radical, then the alkenyl radical is cyclized and added to another benzene ring by 7-endo-trig to realize the construction of seven-membered ring, and finally the dibenzocycloheptane analogue is obtained by deprotonation.

3 Claims, 10 Drawing Sheets

METHOD FOR SYNTHESIZING DIBENZOCYCLOHEPTANE DERIVATIVES BY SERIES CYCLIZATION OF FREE RADICALS UNDER ELECTROOXIDATION CONDITIONS

CROSS-REFERENCE TO RELATED APPLICATIONS

This application claims priority to Chinese Patent Application No. 202111418200.5, filed on Nov. 26, 2021, the contents of which are hereby incorporated by reference.

TECHNICAL FIELD

The present application relates to the technical field of organic synthesis, and in particular to a method for synthesizing dibenzocycloheptane derivatives by series cyclization of free radicals under electrooxidation conditions.

BACKGROUND

The 6-7-6 and polycyclic structures are found in molecules of some pharmaceutical or natural products; among the products, colchicine, the most representative one, is a very important alkaloid with various physiological activities; dibenzocycloheptane is the core skeleton of colchicine, and such a structure has received great attention in organic synthesis and drug development, with examples including NSC51046, ZD6126 and N-acetylcoichine as shown in the following formulas:

NSC 51046

ZD 6126

N-acetylcolchine

Colchicine is an important alkaloid found in Liliaceae plant *Colchicum autumnale*; studies have found that colchicine combines with tubulin dimer to prevent tubulin conversion, so as to stop cells in metaphase of mitosis and causing cell death, and can therefore be utilized in treating Mediterranean fever syndrome, acute gout and other diseases; moreover, colchicine also has good anti-tumor activity and good performance in chemotherapy; among the examples, NSC51046 shows stronger tubulin binding activity and less toxicity as well as less side effects than colchicine, and hence be reckoned as one of the rather promising candidates for preparing anti-tumor drugs; in addition to that, ZD6126 also exhibit strong anticancer activity by inhibiting tubulin polymerization.

Accordingly, the search for new and rather green and efficient methods for synthesizing dibenzocycloheptane derivatives is a task of great challenge and research value.

SUMMARY

The present application aims to provide a method for synthesizing dibenzocycloheptane derivatives by series cyclization of free radicals under electrooxidation conditions.

To achieve the above objectives, the present application provides technical scheme as follows:

one of the technical schemes of the present application is to provide a method for synthesizing dibenzocycloheptane derivatives by series cyclization of free radicals under electrooxidation conditions, including:

using o-propionyl biphenyl analogues and sodium benzenesulfinate analogues as raw materials, electrifying and reacting the raw materials in electrolytic cell to obtain dibenzocycloheptane derivatives;

the o-propionyl biphenyl analogues have structures as shown in the following formula (I):

(I)

where Ar represents an aromatic ring;
$R^1$ is H, alkyl, halogen, ester, nitro, cyano or alkoxy; and
$R^2$ is aryl, alkyl or silicon;
the sodium benzenesulfinate analogues have structures as shown in the following formula (II):

(II)

where R is H, alkyl, halogen atom, nitro, cyano or alkoxy.

Optionally, the aromatic ring includes alkyl, aryl, halogen, or ester-substituted benzene ring, furan, pyrrole or thiophene.

More optionally, the aromatic ring is an alkyl-substituted benzene ring.

Optionally, $R^1$ is alkyl or alkoxy.

Optionally, $R^2$ is aryl.

Optionally, the o-propionyl biphenyl analogues are in a molar ratio of 1: (1-3) to the sodium benzenesulfinate analogues.

Optionally, the electrolytic cell includes electrolyte solution in a concentration of 0.1 mole per liter (mol/L), where the electrolyte solution includes tetrabutylammonium tetrafluoroborate, lithium tert-butoxide, tetrabutylammonium iodate, tetraethylammonium perchlorate, tetraethylammonium hexafluorophosphate or tetrabutylammonium perchlorate as electrolyte; the electrolyte solution also includes at least one of acetonitrile, water, dichloroethane, methanol, isopropanol, ethyl acetate, N,N-dimethylformamide and tetrahydrofuran as solvent;

More optionally, the electrolyte is tetraethylammonium perchlorate, and the solvent is a mixed solvent of acetonitrile and water, where the acetonitrile is in a volume ratio of 3:1 to the water.

Optionally, the electrolytic cell includes carbon electrode graphite felt as anode, and platinum or nickel as cathode.

Optionally, the electrifying and reacting is carried out under reaction temperature of 25-70 degree Celsius (° C.), constant current of 3 milliampere (mA)-10 mA, and reaction duration of 4-10 hours (h).

More optionally, the reaction temperature of the electrifying and reacting is 50° C., the constant current is 4 mA, and the reaction duration is 6 h.

It should be noted that too high a reaction temperature will increase side reactions and too low a reaction temperature will reduce a yield of the target product.

The present application utilizes o-propionyl biphenyl analogues in a mixed solvent prepared form acetonitrile and water to interact with sodium benzenesulfinate analogues, a benzenesulfonyl radical (Ts) precursor, to obtain dibenzocycloheptanes analogues by radical tandem cyclization under anodic oxidation conditions in an electrolytic cell; by using sodium p-toluenesulfinate to describe free radical source as an example, the dibenzocycloheptanes is prepared according to the following reaction formula:

in the above reaction, o-propionyl biphenyl analogues react with sodium benzenesulfinate analogues under current-passing conditions in electrolyte and solvent to obtain dibenzocycloheptane analogues, and the reaction is speculated as follows:

firstly, sodium p-toluenesulfonate ion undergoes oxidation reaction at the anode, and lose electron to generate sodium p-toluenesulfonyl radical; the radical attacks biphenyl at carbon number of carbonyl α-alkynyl to generate a thermodynamically more stable free radical A; then the free radical A is cyclized and added to a benzene ring by 7-endo-trig to form a new free radical B, and the new free radical B lose another electron to generate aryl cation C, followed by deprotonation to form dibenzocycloheptane analogues.

Another technical scheme of the present application is to provide a dibenzocycloheptane derivative synthesized by the above method.

The application has the following beneficial technical effects:

according to the application, under the condition of constant current and electrolyte, benzenesulfinate anion is oxidized into benzenesulfonyl radical; the radical attacks α-position of alkynone reactant carbonyl to obtain an alkenyl radical, then the alkenyl radical is cyclized and added to another benzene ring by 7-endo-trig to realize the construction of seven-membered ring, and finally the dibenzocycloheptane analogue is obtained by deprotonation.

DETAILED DESCRIPTION OF THE EMBODIMENTS

Now various exemplary embodiments of the present application will be described in detail. This detailed description should not be taken as a limitation of the present application, but should be understood as a more detailed description of some aspects, characteristics and embodiments of the present application. It should be understood that the terms mentioned in the present application are only used to describe specific embodiments, and are not used to limit the present application.

In addition, for the numerical range in the present application, it should be understood that each intermediate value between the upper limit and the lower limit of the range is also specifically disclosed. Any stated value or intermediate value within the stated range, and any other stated value or intermediate value within the stated range are also included in the present application. The upper and lower limits of these smaller ranges can be independently included or excluded from the range.

Unless otherwise stated, all technical and scientific terms used herein have the same meanings commonly understood by those of ordinary skill in the field to which this application relates. Although the present application only describes preferred methods and materials, any methods and materials similar or equivalent to those described herein can be used in the practice or testing of the present application.

As used in this paper, the terms "comprising", "including", "having" and "containing" are all open terms, meaning including but not limited to.

Embodiment 1

O-propionyl biphenyl 1a (102.6 milligram (mg), 0.3 millimole (mmol), 1.0 equivalent (equiv.)), sodium p-toluenesulfonate 2a (106.8 mg, 0.6 mmol, 2.0 equiv.) and tetraethylammonium perchlorate (92 mg, 0.4 mmol, 0.1 mole per liter (M)) are accurately added into a reaction tube, and a mixed solvent MeCN/H$_2$O (volume/volume, v/v, 3:1, 4 milliliters (mL)) is added into the tube at last, followed by reaction at 50 degree Celsius (° C.) for 6 hours (h) under constant current; then all solvents are transferred to a round bottom flask, then the flask is added with silica and subjects to evaporation in vacuum; n-hexane/EtOAc (v/v, 3:1) is taken as eluent, then a corresponding product 3a is obtained by silica gel column chromatography with a yield of 75%, and the reaction is as follows:

Nuclear magnetic resonance (NMR) data of the product: $^1$H NMR (600 megahertz (MHz), CDCl$_3$) δ7.87 (d, J=7.9 Hz, 1 H), 7.68 (td, J=7.6, 1.6 Hz, 1 H), 7.57-7.52 (m, 2 H), 7.19 (t, J=7.4 Hz, 2 H), 7.09 (d, J=8.3 Hz, 3 H), 6.95 (d, J=8.1 Hz, 2 H), 6.71 (d, J=2.4 Hz, 1 H), 6.32 (d, J=2.4 Hz, 1 H), 3.85 (s, 3 H), 3.20 (s, 3 H), 2.30 (s, 3 H). $^{13}$C NMR (151 MHz, CDCl$_3$) δ193.6, 161.3, 160.7, 146.9, 145.1, 143.5, 142.2, 140.3, 138.9, 138.3, 135.8, 131.2, 128.9, 128.8, 128.1, 128.0, 127.9, 126.8, 125.5, 118.3, 106.9, 99.6, 55.6, 55.6, 21.6. HR-MS(ESI)m/z calc. for C$_{30}$H$_{25}$O$_5$S[M+H]$^+$:497.1417, found: 497.1398.

Figure 1:
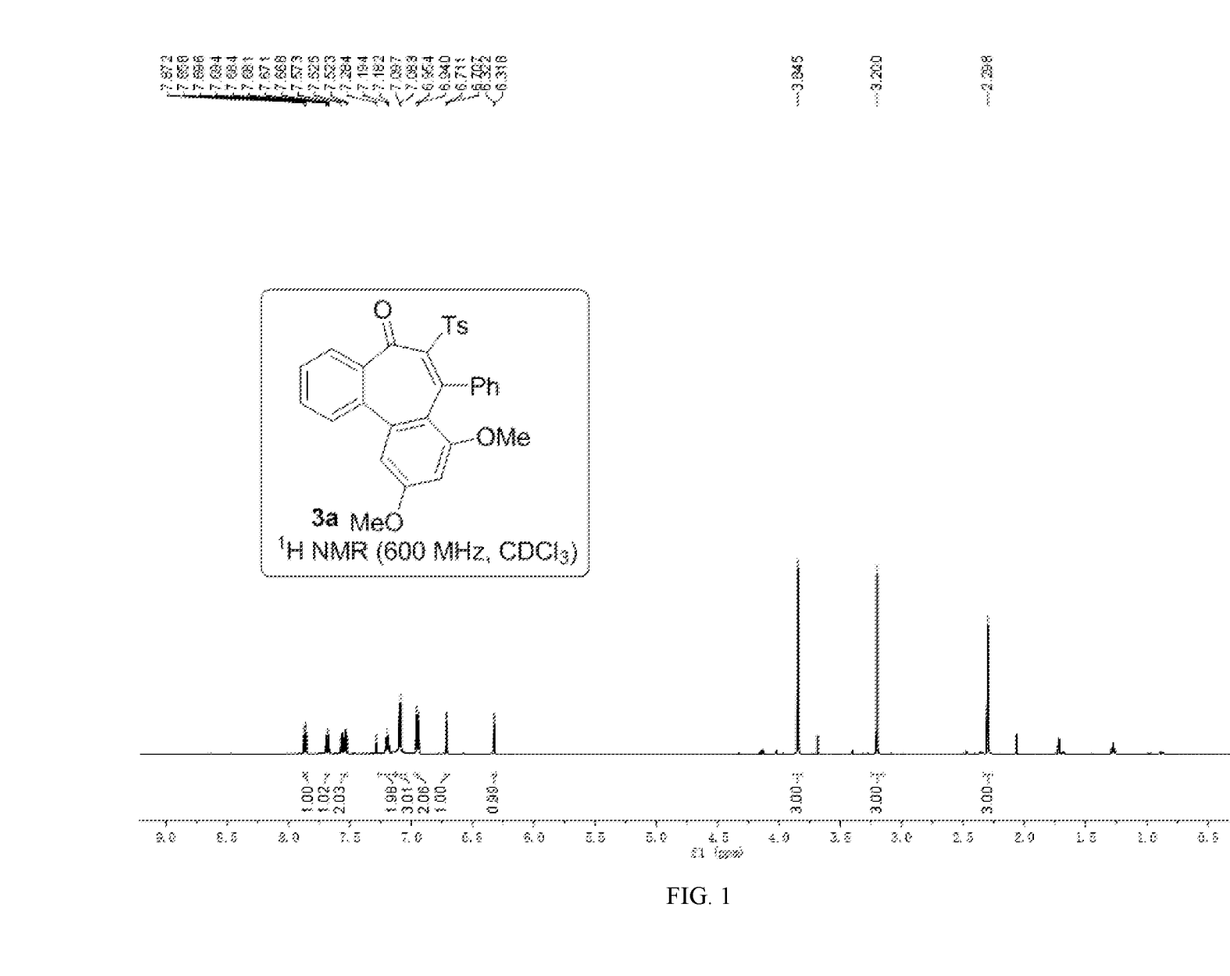
FIG. 1 shows an $^1$H NMR spectrum of a product prepared in Embodiment 1.
Figure 2:
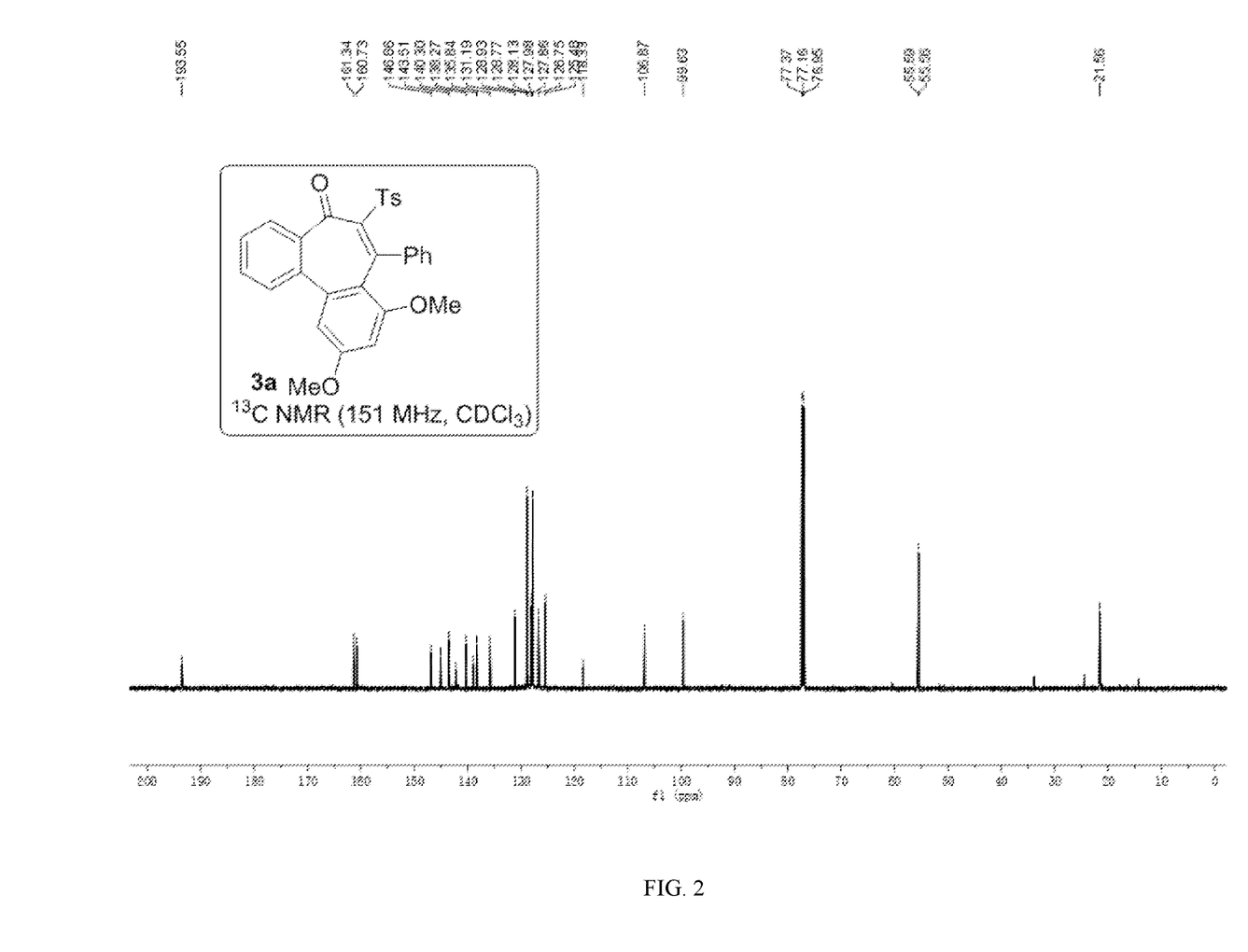
FIG. 2 shows a $^{13}$C NMR spectrum of the product prepared in Embodiment 1.

See FIG. 1 for the $^1$H NMR spectrum of the product prepared in Embodiment 1, and FIG. 2 for the $^{13}$C NMR spectrum of the product prepared in Embodiment 1.

Embodiment 2

O-propionyl biphenyl 1b (115.8 mg, 0.3 mmol, 1.0 equiv.), sodium p-toluenesulfonate 2a (106.8 mg, 0.6 mmol, 2.0 equiv.), tetraethylammonium perchlorate (92 mg, 0.4 mmol, 0.1 M) are accurately added into a reaction tube, and a mixed solvent Mecn/H₂O (v/v, 3:1, 4 mL) is added into the tube at last, followed by reaction at 50° C. for 6 h under constant current; then all the reagents are transferred to a round bottom flask, and the round bottom flask is added with silica and subjects to evaporation in vacuum; n-hexane/EtOAc (v/v, 3:1) is used as eluent, then a corresponding product 3b is obtained by silica gel column chromatography with a yield of 43.2%, where the reaction is as follows:

constant current; then all solvents are transferred into a round bottom flask, and the flask is added with silica and then subjects to evaporation in vacuum; n-hexane/EtOAc (v/v, 3:1) is used as eluent, and a corresponding product 3c is obtained by silica gel column chromatography with a yield of 47.1%, where the reaction is as follows:

NMR data of the product: $^{1}$H NMR (600 MHz, CDCl₃) δ7.84 (d, J=7.9 Hz, 1 H), 7.71-7.65 (td, J=6.6, 2.4 Hz, 1 H), 7.57-7.54 (m, 2 H), 7.17 (d, J=8.1 Hz, 2 H), 7.00 (d, J=8.1 Hz, 2 H), 6.71 (d, J=2.4 Hz, 1 H), 6.59 (d, J=6.1 Hz, 2 H), 6.35 (d, J=2.3 Hz, 2 H), 5.90 (d, J=29.2 Hz, 2 H), 3.86 (s, 3 H), 3.35 (s, 3 H), 2.32 (s, 3 H). 13 C NMR (101 MHz, CDCl₃)δ193.6, 161.4, 160.9, 147.5, 146.5, 146.2, 145.2, 143.6, 142.2, 140.4, 139.1, 135.9, 132.2, 131.2, 128.9, 128.8, 128.1, 128.0, 125.7, 118.0, 107.1, 106.8, 101.1, 99.5, 55.8, 55.6, 21.6.HR-MS(ESI)m/z calc.for $C_{30}H_{25}O_5S[M+H]^{+}$:541.1316, found: 541.1293.

Figure 3:
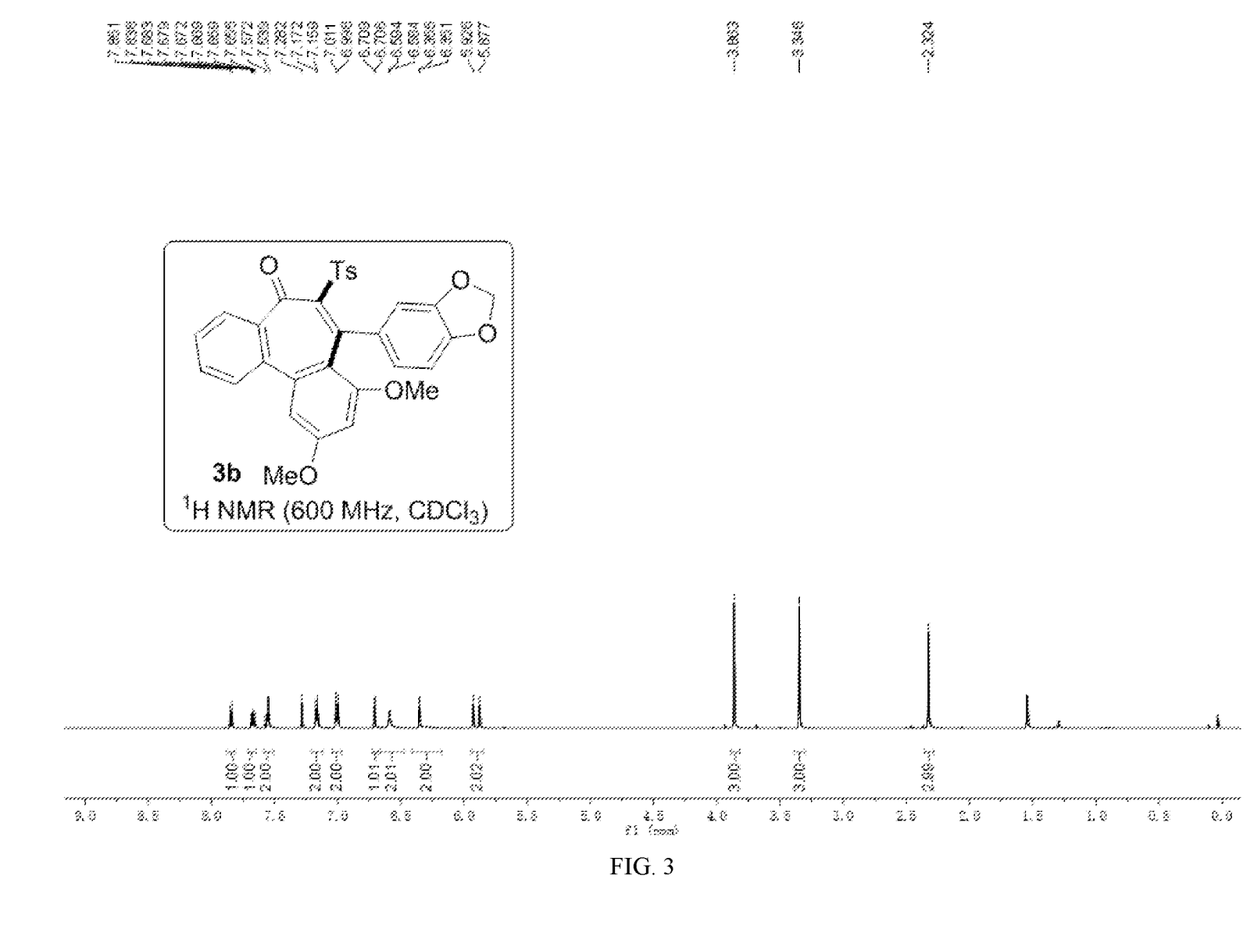
FIG. 3 shows an $^1$H NMR spectrum of a product prepared in Embodiment 2.
Figure 4:
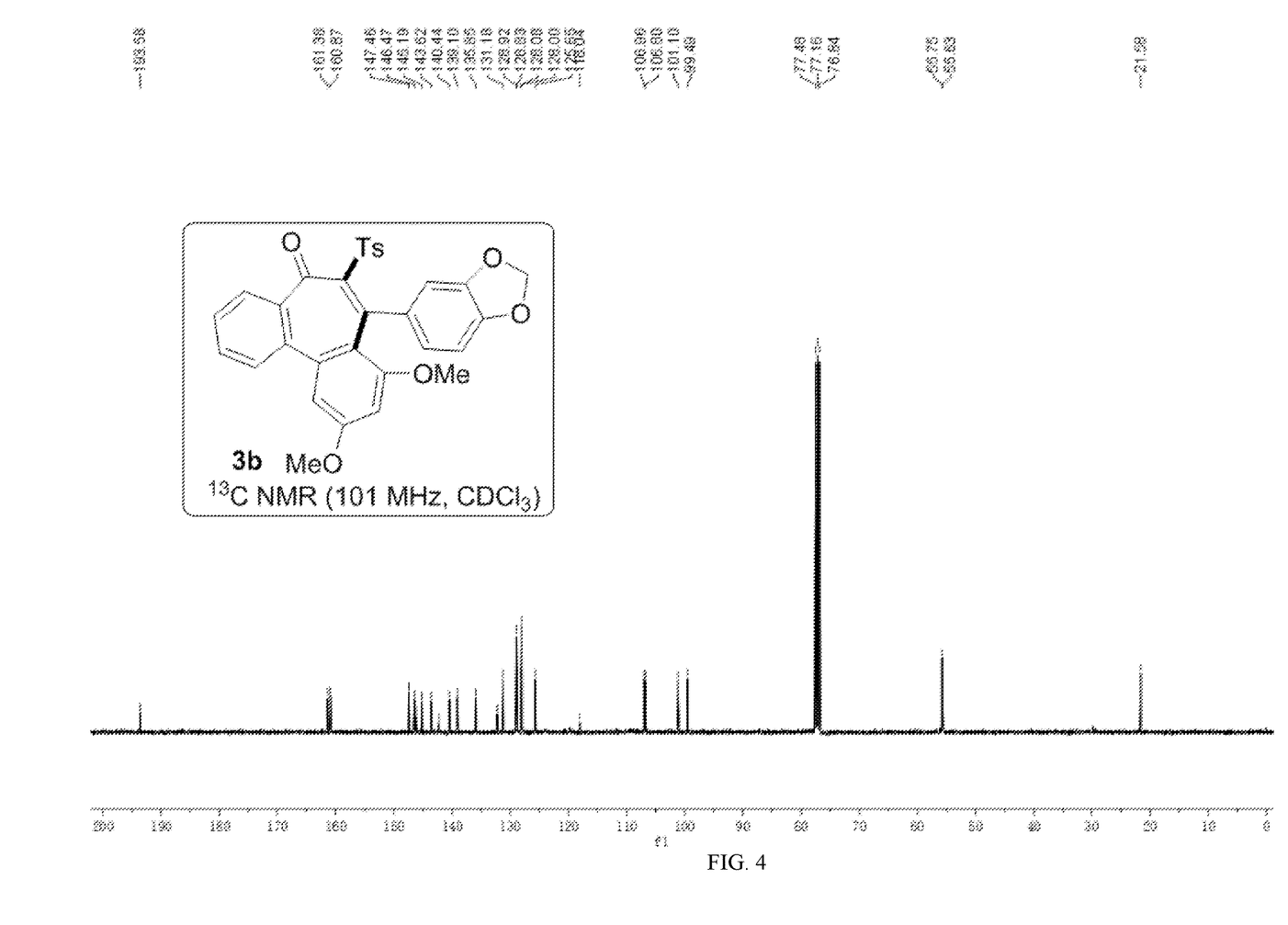
FIG. 4 shows a $^{13}$C NMR spectrum of the product prepared in Embodiment 2.

FIG. 3 shows the $^{1}$H NMR spectrum of the product prepared in Embodiment 2, and FIG. 4 illustrates the $^{13}$C NMR spectrum of the product prepared in Embodiment 2.

Embodiment 3

O-propionyl biphenyl 1c (106.8 mg, 0.3 mmol, 1.0 equiv.), sodium p-toluenesulfonate 2a (106.8 mg, 0.6 mmol, 2.0 equiv.) and tetraethylammonium perchlorate (92 mg, 0.4 mmol, 0.1 M) are accurately added into a reaction tube, then a mixed solvent Mecn/H₂O ((v/v, 3:1, 4 mL) is added into the tube at last, followed by reaction at 50° C. for 6 h under

NMR data of the product: $^{1}$H NMR (600 MHz, CDCl₃) δ7.88(d, J=7.8 Hz, 1 H), 7.69 (td, J=7.2, 1.8 Hz, 1 H), 7.61-7.56 (m, 2 H), 7.11-7.05 (m, 3 H), 7.00-6.96 (m, 3 H), 6.72 (d, J=2.4 Hz, 1 H), 6.33 (d, J=2.4 Hz, 1 H), 3.85 (s, 3 H), 3.21 (s, 3 H), 2.31-2.14 (m, 6 H). $^{13}$C NMR (151 MHz, CDCl₃) δ193.6, 161.3, 160.8, 147.1, 145.1, 143.3, 142.2, 140.3, 139.2, 138.1, 136.2, 135.8, 131.2, 128.9, 128.8, 128.7, 128.2, 127.8, 126.7, 125.5, 118.3, 106.9, 99.7, 55.7, 55.6, 21.5, 21.2. HR MS(ESI) m/z calc.for $C_{31}H_{27}O_5S[M+H]^{+}$:511.1574, found: 511.1580.

Figure 5:
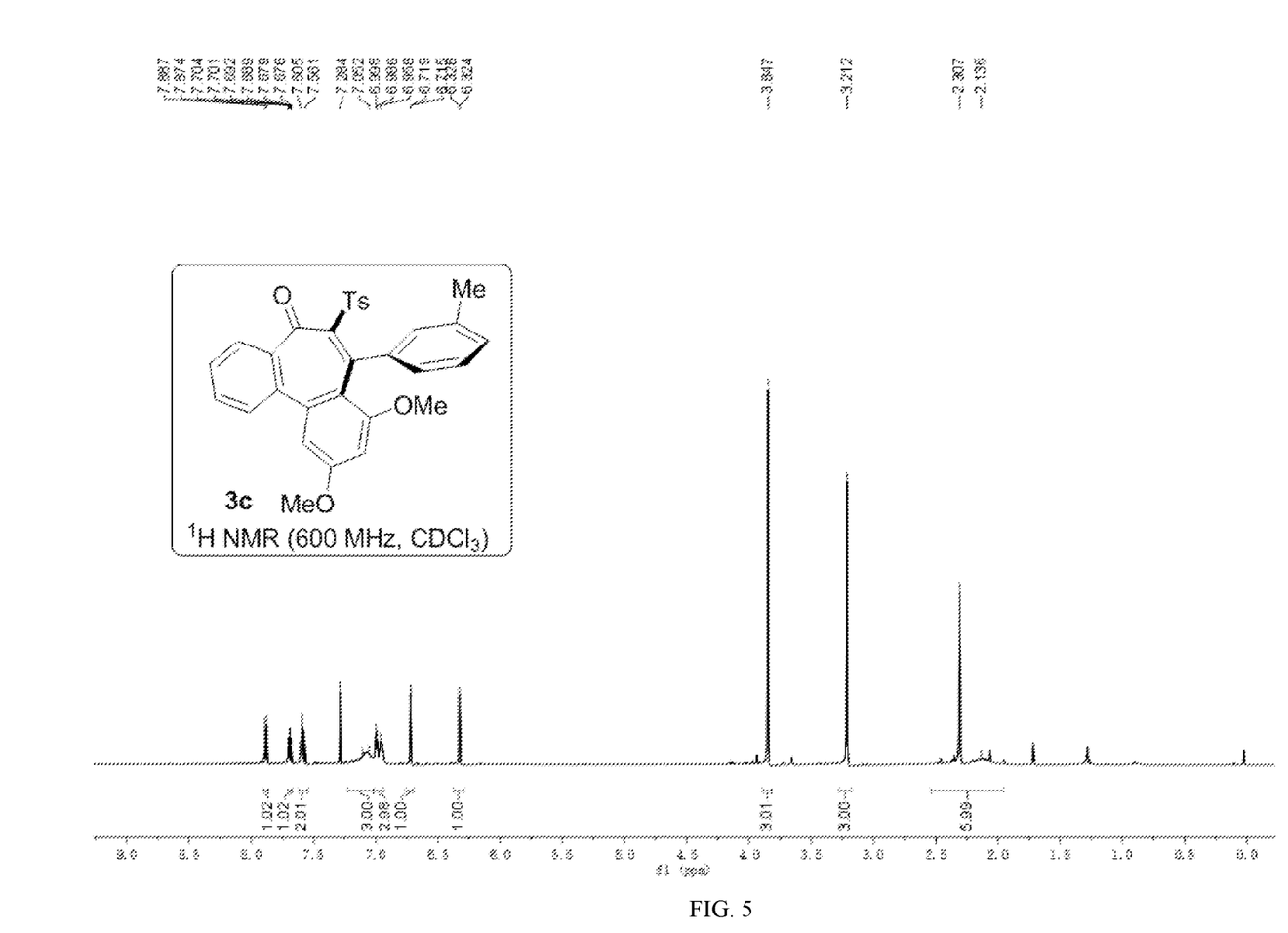
FIG. 5 shows an $^1$H NMR spectrum of a product prepared in Embodiment 3.
Figure 6:
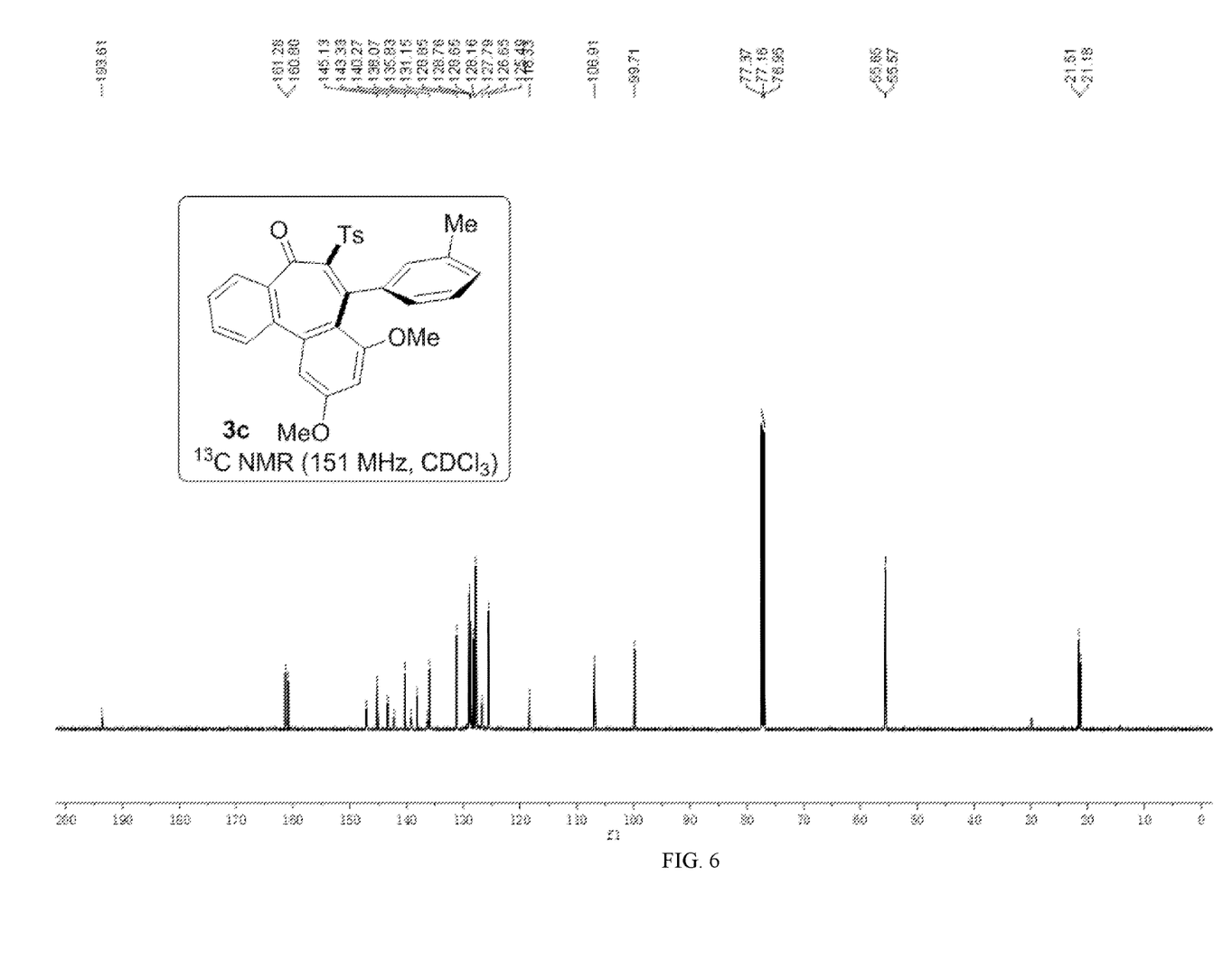
FIG. 6 shows a $^{13}$C NMR spectrum of the product prepared in Embodiment 3.

See FIG. 5 for the $^{1}$H NMR spectrum of the product prepared in Embodiment 3, and FIG. 6 for the $^{13}$C NMR spectrum of the product prepared in Embodiment 3.

Embodiment 4

O-propionyl biphenyl 1d (112.8 mg, 0.3 mmol, 1.0 equiv.), sodium p-toluenesulfonate 2a (106.8 mg, 0.6 mmol, 2.0 equiv.) and tetraethylammonium perchlorate (92 mg, 0.4 mmol, 0.1 M) are accurately added into a reaction tube, then a mixed solvent Mecn/H₂O (v/v, 3:1, 4 mL) is added into the tube at last, followed by reaction at 50° C. for 6 h under constant current; then all solvents are transferred to a round bottom flask, and the flask is added with silica and subjects to evaporation in vacuum; n-hexane/EtOAc (v/v, 3:1) is used as eluent, and a corresponding product 3d is obtained by silica gel column chromatography with a yield of 50.3%, where the reaction is as follows:

1d

3d

NMR data of the product: $^1$H ENMR (400 MHz, CDCl$_3$) δ7.85 (d, J=1.9 Hz, 1 H), 7.54 (dd, J=8.2, 1.9 Hz, 1 H), 7.46 (d, J=8.2 Hz, 1 H), 7.28-7.12 (m, 5 H), 7.01 (d, J=8.1 Hz, 2 H), 6.68 (d, J=2.4 Hz, 1 H), 6.34 (d, J=2.4 Hz, 1 H), 3.87 (s, 3 H), 3.20 (s, 3 H), 2.33 (s, 3 H). $^{13}$C NMR (101 MHz, CDCl$_3$) δ192.6, 161.5, 160.8, 147.0, 143.8, 143.4, 142.3, 138.9, 138.9, 138.1, 137.5, 137.2, 129.1, 128.8, 128.2, 128.1, 128.0, 127.0, 126.8, 118.4, 106.8, 100.1, 55.7, 55.6, 21.6.HR-MS (ESI)m/z calc.for C$_{30}$H$_{24}$ClO$_5$S[M+H]$^+$: 531.1028, found: 531.1008.

Figure 7:
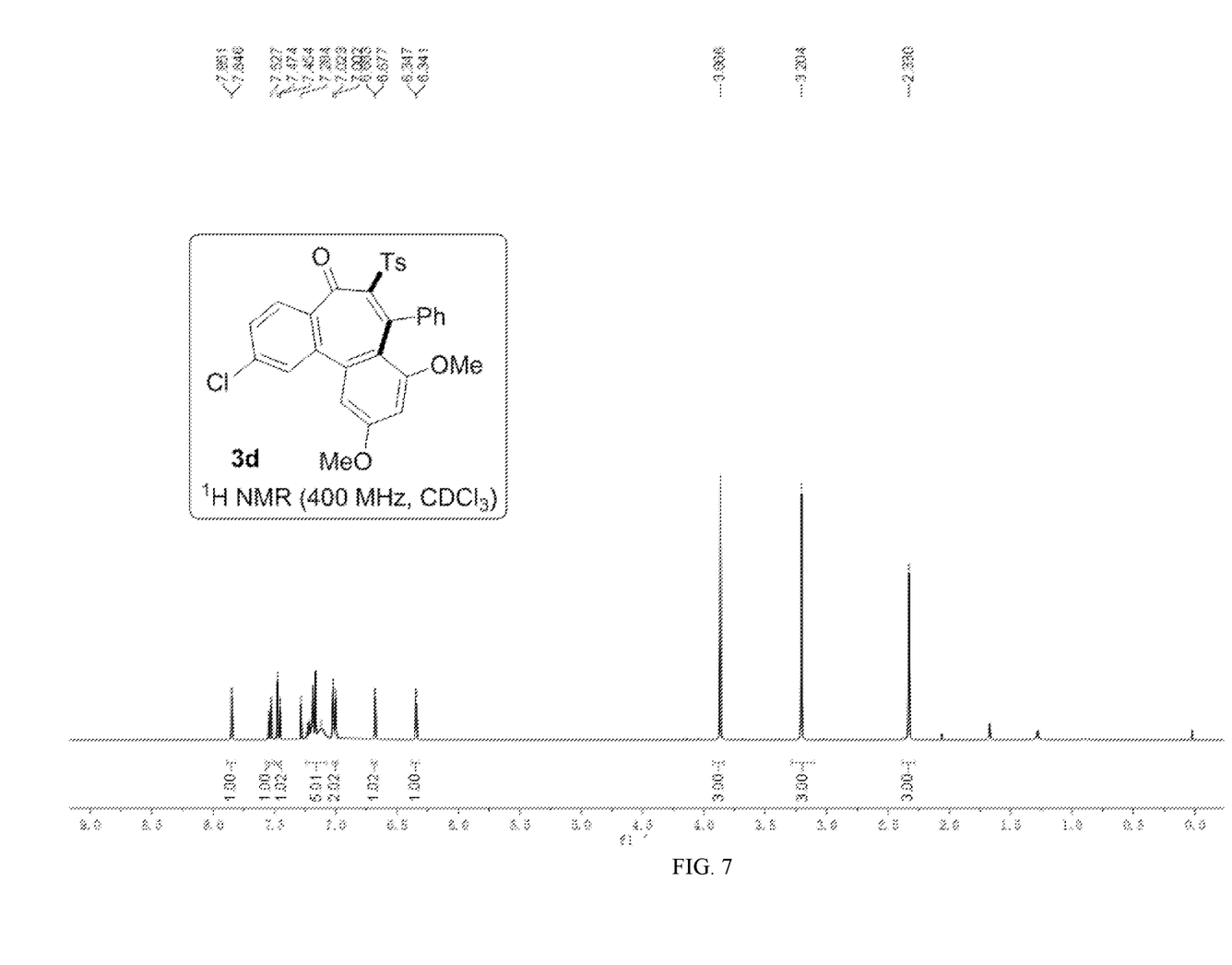
FIG. 7 shows an $^1$H NMR spectrum of a product prepared in Embodiment 4.
Figure 8:
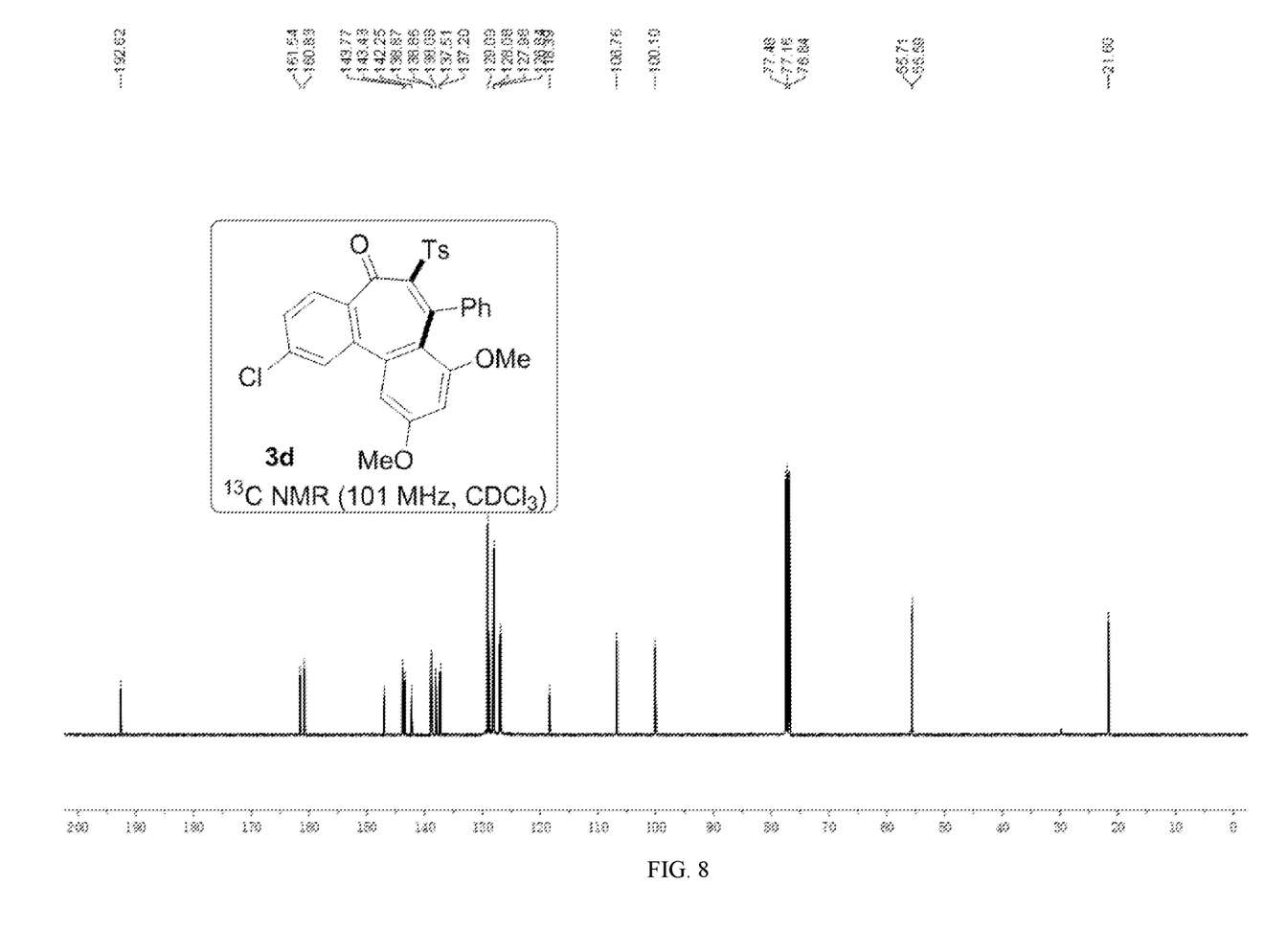
FIG. 8 shows a $^{13}$C NMR spectrum of the product prepared in Embodiment 4.

The $^1$H NMR spectrum of the product prepared in Embodiment 4 is illustrated in FIG. 7, and the $^{13}$C NMR spectrum of the product prepared in Embodiment 4 is shown in FIG. 8.

Embodiment 5

O-propionyl biphenyl 1e (104.4 mg, 0.3 mmol, 1.0 equiv.), sodium p-toluenesulfonate 2a (106.8 mg, 0.6 mmol, 2.0 equiv.), tetraethylammonium perchlorate (92 mg, 0.4 mmol, 0.1 M) are accurately added into a reaction tube, and a mixed solvent Mecn/H$_2$O is added into the tube at last, followed by reaction at 50° C. for 6 h under constant current; then all solvents are transferred in to a round bottom flask, and the flask is added with silica and subjects to evaporation in vacuum; n-hexane/EtOAc(v/v, 3:1) is used as eluent, and a corresponding product 3e is obtained by silica gel column chromatography with a yield of 55.8%, where the reaction is as follows:

1e

3e

NMR data of the product: $^1$H NMR (600 MHz, CDCL$_3$) δ7.64 (dd, J=29.6, 5.1 Hz, 2 H), 7.45 (d, J=8.2 Hz, 2 H), 7.28-7.24 (m, 2 H), 7.11 (d, J=8.3 Hz, 3 H), 6.84 (d, J=2.4 Hz, 1 H), 6.32 (d, J=2.3 Hz, 1 H), 3.87 (s, 3 H), 3.12 (s, 3 H), 2.36 (s, 3 H). $^{13}$C NMR (151 MHz, CDC:$_3$) δ184.1, 162.1, 161.9, 147.4, 143.9, 143.6, 140.9, 140.3, 139.8, 139.0, 135.7, 130.7, 129.1, 128.5, 128.1, 127.0, 119.0, 104.7, 99.7, 55.6, 55.5, 21.6. HR-MS (ESI) m/z calc. for C$_{28}$H$_{24}$ClO$_5$S[M+H]$^+$:503.0982, found: 503.0986.

Figure 9:
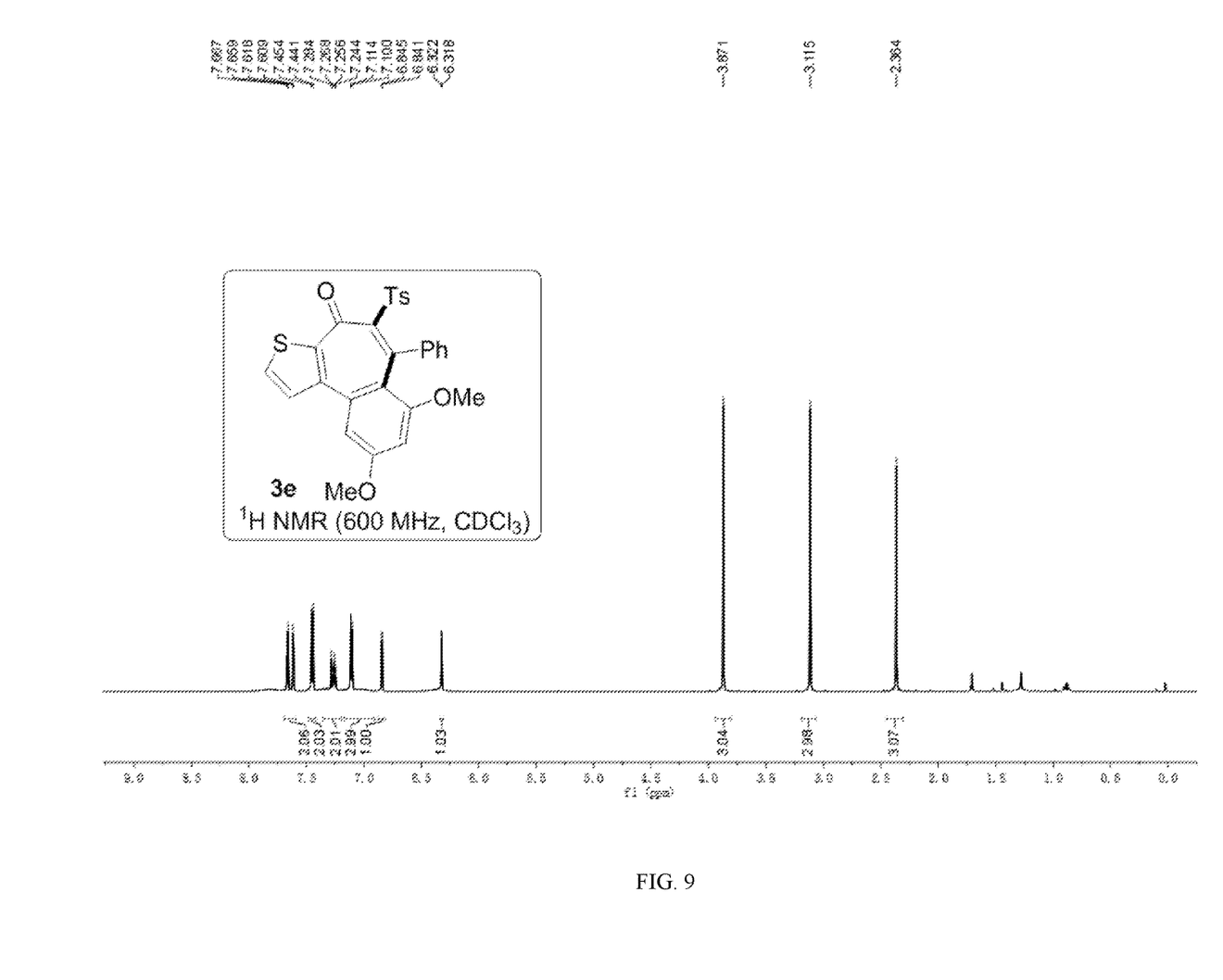
FIG. 9 shows a $^1$H NMR spectrum of a product prepared in Embodiment 5.
Figure 10:
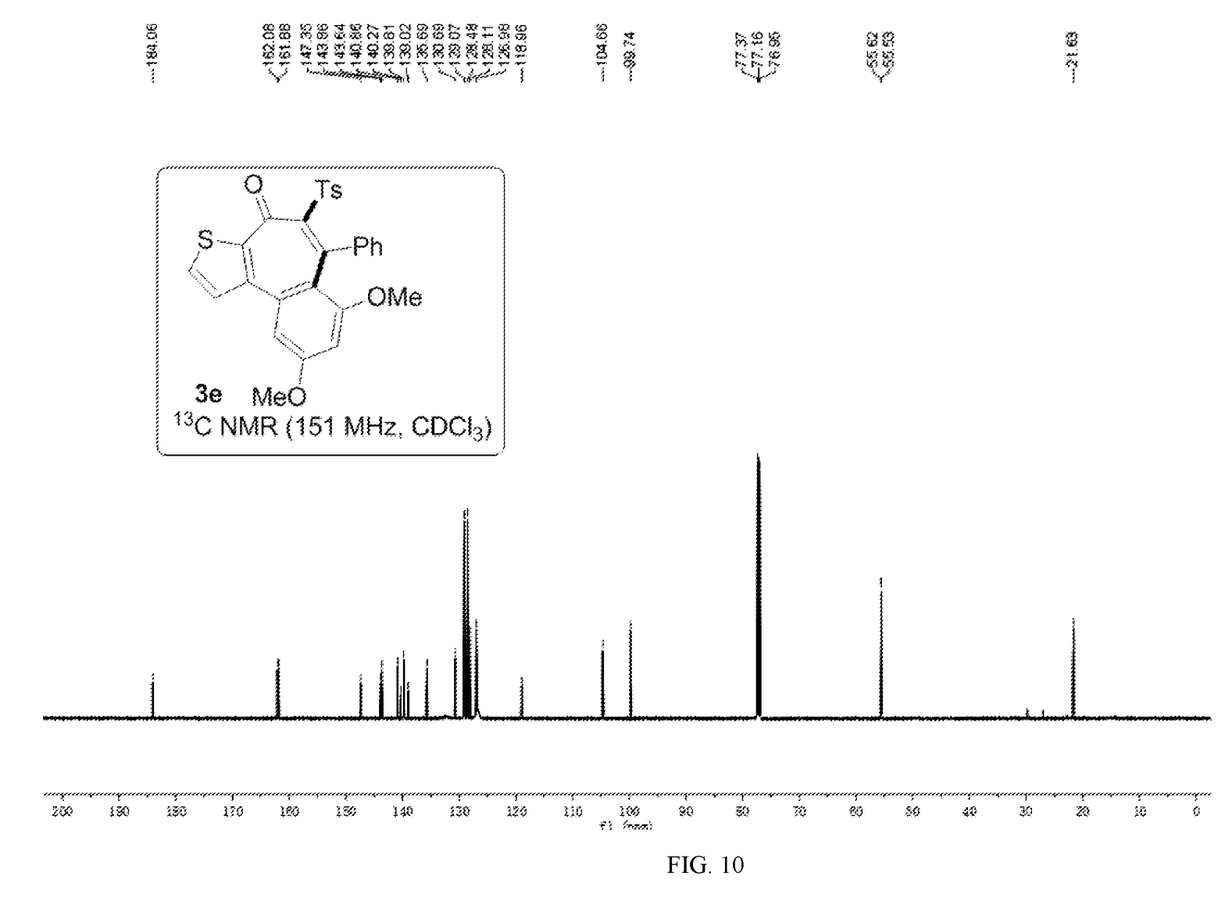
FIG. 10 shows a $^{13}$C NMR spectrum of the product prepared in Embodiment 5.

FIG. 9 shows the $^1$H NMR spectrum of the product prepared in Embodiment 5, and FIG. 10 shows the $^{13}$C NMR spectrum of the product prepared in Embodiment 5.

Embodiment 6

The reaction of the present embodiment is optimized with conditions as follows:

O-propionyl biphenyl 1a (0.3 mmol, 1.0 equiv.), sodium p-toluenesulfonate 2a (0.9 mmol, 3.0 equiv.), electrolyte 0.1 M and solvent 4 mL are added into a reaction tube, followed by reaction for 6 h under constant current of 4 milliampere (mA) with graphite felt (GF) as anode and platinum (Pt) as cathode; then all solvents are transferred into a round bottom flask, then the flask is added with silica and subjects to evaporation in vacuum; n-hexane/EtOAc (v/v, 3:1) is used as eluent, then a product 3a is obtained by silica gel column chromatography, and the yield is calculated, where the reaction is as follows:

See Table 1 for parameter optimization process and yield.

TABLE 1

|  | Solvent (v/v) | Electrolyte | Temperature (° C.) | Yield (%) |
| --- | --- | --- | --- | --- |
| 1 | EtOH/H$_2$O (3:1) | Et$_4$NClO$_4$ | 50 | 0 |
| 2 | DMF/H$_2$O (3:1) | Et$_4$NClO$_4$ | 50 | 0 |
| 3 | 1,4-Dioxane/H$_2$O (3:1) | Et$_4$NClO$_4$ | 50 | 39 |
| 4 | DCE/MeCN/H$_2$O (5:5:1) | Et$_4$NClO$_4$ | 50 | 37 |
| 5 | MeCN/H$_2$O (3:1) | Et$_4$NClO$_4$ | 50 | 73 |
| 6 | MeCN/H$_2$O (3:1) | n-Bu$_4$NI | 50 | 32 |
| 7 | MeCN/H$_2$O (3:1) | n-Bu$_4$NPF$_6$ | 50 | 56 |
| 8 | MeCN/H$_2$O (3:1) | n-Bu$_4$NBF$_4$ | 50 | 64 |
| 9 | MeCN/H$_2$O (3:1) | n-Bu$_4$NClO$_4$ | 50 | 43 |
| 10 | MeCN/H$_2$O (3:1) | — | 50 | 59 |
| 11[a] | MeCN/H$_2$O (3:1) | Et$_4$NClO$_4$ | 50 | 68 |
| 12 | MeCN/H$_2$O (3:1) | Et$_4$NClO$_4$ | 25 | 0 |
| 13 | MeCN/H$_2$O (3:1) | Et$_4$NClO$_4$ | 60 | 50 |
| 14[b] | MeCN/H$_2$O (3:1) | Et$_4$NClO$_4$ | 50 | 32 |
| 15[c] | MeCN/H$_2$O (3:1) | Et$_4$NClO$_4$ | 50 | 60 |
| 16[d] | MeCN/H$_2$O (3:1) | Et$_4$NClO$_4$ | 50 | 54 |
| 17[e] | MeCN/H$_2$O (3:1) | Et$_4$NClO$_4$ | 50 | 0 |
| 18[f] | MeCN/H$_2$O (3:1) | Et$_4$NClO$_4$ | 50 | 0 |

As can be seen from Table 1, [a] indicates that an addition amount of sodium p-toluenesulfonate 2a is 0.9 mmol, 3.0 equiv., [b] means a constant current of 3 mA, [c] indicates a constant current of 6 mA, [d] indicates GF as anode and nickel (Ni) as cathode, [e] represents Pt as anode and Pt as cathode, and [f] means no electricity.

The above-mentioned embodiments only describe the preferred mode of the application, but do not limit the scope of the application. On the premise of not departing from the design spirit of the application, all kinds of modifications and improvements made by ordinary technicians in the field to the technical scheme of the application shall fall within the scope of protection determined by the claims of the application.

What is claimed is:

1. A method for synthesizing dibenzocycloheptenone having a formula (III) by series cyclization of free radicals under electrooxidation conditions, comprising:
   electrifying and reacting the raw materials in an electrolytic cell followed by deprotonation to obtain dibenzocycloheptenone as shown in the following path, wherein the compound having a formula (I) and sodium benzenesulfinate are used as raw materials;

wherein:

(I)

in the formula (I), Ar is an alkyl or a halogen-substituted benzene ring;

$R^1$ is selected from the group consisting of H, alkyl, halogen atom, ester, and alkoxy; and $R^2$ is aryl;

the sodium benzenesulfinate have a structure as shown of formula (II):

(II)

in the formula (II), R is H, alkyl, halogen atom, nitro, cyano or alkoxy;

electrolyte solution in the electrolytic cell has a concentration of 0.1 mole per liter (mol/L); the electrolyte solution includes tetraethylammonium perchlorate as electrolyte, the electrolyte solution also includes a compound solvent of acetonitrile and water as solvents, and the acetonitrile is in a volume ratio of 3:1 to the water; and the electrolytic cell includes a carbon electrode graphite felt as an anode, and platinum or nickel as a cathode; and the electrifying and reacting is carried out under a reaction temperature of 50 degree Celsius (° C.), a constant current of 4 milliampere (mA), and a reaction duration of 6 hours (h).

2. The method for synthesizing dibenzocycloheptenone according to claim 1, wherein in the formula (I) Ar is an alkyl-substituted benzene ring.

3. The method for synthesizing dibenzocycloheptenone according to claim 1, wherein in the formula (I) the $R^1$ is alkyl or alkoxy.

\* \* \* \* \*